United States Patent
Harrison et al.

(10) Patent No.: US 9,526,652 B2
(45) Date of Patent: *Dec. 27, 2016

(54) DEVICE AND METHOD FOR CORRECTING OBSTRUCTIVE SLEEP APNEA

(71) Applicant: The Regents of the University of California, Oakland, CA (US)

(72) Inventors: Michael R. Harrison, San Francisco, CA (US); Kathryn H. Rosenbluth, San Francisco, CA (US); Dillon A. Kwiat, San Francisco, CA (US); Eric J. Kezirian, Los Angeles, CA (US); Richard J. Fechter, San Rafael, CA (US); Darrell Christensen, Petaluma, CA (US)

(73) Assignee: The Regents of the University of California, Oakland, CA (US)

( * ) Notice: Subject to any disclaimer, the term of this patent is extended or adjusted under 35 U.S.C. 154(b) by 177 days.

This patent is subject to a terminal disclaimer.

(21) Appl. No.: 14/598,436

(22) Filed: Jan. 16, 2015

(65) Prior Publication Data

US 2015/0144142 A1    May 28, 2015

Related U.S. Application Data

(63) Continuation-in-part of application No. 14/338,188, filed on Jul. 22, 2014, now abandoned, which is a continuation of application No. 12/930,834, filed on Jan. 18, 2011, now Pat. No. 8,808,158.

(51) Int. Cl.
*A61M 37/00*    (2006.01)
*A61N 2/00*    (2006.01)
*A61F 5/56*    (2006.01)

(52) U.S. Cl.
CPC .................... *A61F 5/566* (2013.01)

(58) Field of Classification Search
CPC .......... A61N 2/00; A61N 2/004; A61N 2/006; A61N 2/002
USPC ........... 600/9–15, 26–28; 128/848, 897–899; 602/902
See application file for complete search history.

(56) References Cited

U.S. PATENT DOCUMENTS

| 7,500,484 B2 | 3/2009 | Nelson |
| 7,644,714 B2 | 1/2010 | Atkinson |
| 8,808,158 B2 * | 8/2014 | Harrison ................... A61F 5/56 128/848 |
| 2015/0031964 A1 * | 1/2015 | Bly ........................ A61B 5/165 600/301 |

(Continued)

*Primary Examiner* — John Lacyk
(74) *Attorney, Agent, or Firm* — Lumen Patent Firm (57) ABSTRACT

An orthotic obstructive sleep apnea treatment device is provided that includes a hyoid bone attachment element disposed to attach a ferric element to a hyoid bone, where the ferric element is disposed to face along a treatment vector from the hyoid bone, and the treatment vector is oriented relative to a sagittal plane of a human. The orthotic obstructive sleep apnea treatment device further includes an external orthotic neck device having a contoured housing with a shape disposed to conform about a neck of the human subject, where the housing includes a force delivery element disposed at an exterior-front neck region of the human subject and is disposed to provide an attractive force to the ferric element along the treatment vector. An accelerometer is disposed to measure kinematic variables or movement.

23 Claims, 6 Drawing Sheets

(56) References Cited

U.S. PATENT DOCUMENTS

2016/0120716 A1* 5/2016 Ribble ................ A61B 5/6892
            5/616

* cited by examiner

DEVICE AND METHOD FOR CORRECTING OBSTRUCTIVE SLEEP APNEA

CROSS-REFERENCE TO RELATED APPLICATIONS

This application is a continuation-in-part of U.S. patent application Ser. No. 14/338,188 filed on Jul. 22, 2014. U.S. patent application Ser. No. 14/338,188 is a continuation of U.S. patent application Ser. No. 12/930,834 filed Jan. 18, 2011, now U.S. Pat. No. 8,808,158 issued on Aug. 19, 2014, which is incorporated herein by reference.

FIELD OF THE INVENTION

The present invention relates generally to a method and device for treatment of sleep disorders. More particularly the invention relates to a method and device for the treatment of snoring, and obstructive sleep apnea.

BACKGROUND OF THE INVENTION

Obstructive sleep apnea ("OSA") is a disorder characterized by repeated upper airway obstruction during sleep. OSA is a serious and life-threatening breathing disorder that affects an estimated 20 million American adults.

OSA is associated with significant adverse impacts on health and daily function including daytime sleepiness, decreases in quality of life, headaches, and serious health effects such as cardiovascular disease (hypertension, myocardial infarction, and cerebrovascular accident), endocrine disease, and death. Men, the elderly, and the obese are at elevated risk. Snoring is a related, albeit less severe, disorder that can be associated with partial airway obstruction, and it affects millions more. Therapies that treat OSA may also be effective treatments for snoring.

Current treatment methods—which range from over-the-counter oral and nasal supports to complicated surgeries—tend to be poorly tolerated and/or of limited effectiveness. These concerns may constitute barriers to diagnosis and treatment. There is a need for better OSA therapies to alleviate the suffering of individuals with OSA and also provide benefits to their families, employers, the medical infrastructure, and society at large.

The market for treatments of OSA and snoring is currently experiencing a period of unprecedented growth due both to the increasing percentage of Americans affected by the risk factors for OSA (obesity, advanced age) and to greater awareness of the conditions by medical providers and patients. As both groups have recognized the consequences of OSA and snoring, there has been a greater focus on diagnosis and treatment.

Sleep is associated with a number of physiologic changes, including the loss of upper airway muscle tone and changes in neuromuscular reflexes that can result in upper airway obstruction and snoring. In many patients with OSA and snoring, the relaxation of muscles and other changes lead to collapse of various structures around the throat and contribute to blockage of breathing and/or vibration of structures.

Current treatments for OSA and snoring include non-invasive solutions that are either only minimally effective (e.g. external nasal dilator strips or jaw-advancing appliances), efficacious but poorly tolerated (e.g. positive airway pressure therapy), or surgery (e.g. uvulopalatopharyngoplasty) that can be ineffective, invasive, costly, associated with substantial side effects, and non-reversible.

Positive Airway Pressure ("PAP") techniques and devices are commonly used in the industry. Useful variations include BiPAP and AutoPAP. PAP is administered by means of a mechanical unit that delivers pressurized room air to the upper airway through an interface (e.g. nasal mask) that is worn by the patient during sleep. Pressurized air functions as a pneumatic splint to maintain airway patency. PAP is highly efficacious, but unfortunately long-term acceptance of this treatment and compliance are often poor. Studies have shown that between 20% and 70% of patients fail to use nasal CPAP as prescribed. Problems associated with PAP include an inability to fall asleep while wearing the device, excessive dryness of the mouth and throat, mucous congestion, sinusitis, and unconscious removal of the device during the night. Nonetheless, the market for CPAP devices is enormous and has sprouted several large companies.

One attempt to address the needs in the art teach using a magnet secured to an endotracheal tube, which is passed though the throat so that the tube can maintain a patient airway. Because the tube is subject to dislodgment, an external neckband containing a magnet was configured to attract the magnet in the tube so that tube is not subject to extubation.

Another attempt to address the needs using magnets include the use of multiple implanted magnets. Problems with prior art attempts when multiple magnets are implanted in a patient include (1) continuous force, (2) proximity will increase magnetic interaction and (3) attractive or repulsive magnetic interaction can result in migration of the magnets. The application of continuous force may be unnecessary (cannot be readily discontinued when an apnea correction is not needed during sleep or while awake) or result in adverse consequences (for example, resulting in changes in voice or difficulty swallowing). In (2) and (3), magnetic attractive force increases as attractively oriented magnets approach each other. For magnets in soft tissue, this can lead to an accelerating process, with greater increases in attractive forces as the distance between the magnets decreases. Such attractive forces will increase the tendency of such attractive magnets to migrate, exacerbating this problem.

Other non-surgical treatments for sleep apnea include the use of mandibular repositioning devices and other oral appliances that hold and/or pull the jaw or tongue in a forward position to open the airway by reducing collapse of the soft palate, tongue, and/or other structures. These devices also suffer from uneven compliance rates and can be associated with changes in dental occlusion, dental pain, and inflammatory or degenerative changes in the temporomandibular joint.

Surgical procedures can be performed to treat OSA and snoring, and the selection is based on a number of factors, including the procedure's benefits and the individual patient's pattern of upper airway obstruction, whether at the palate and/or tongue (aka retrolingual, retroglossal, or hypopharyngeal) regions. Tracheotomy was the first OSA treatment; although highly effective, tracheotomy carries untoward social, and in some cases medical, side effects and is not performed commonly for OSA treatment. Uvulopalatopharyngoplasty ("UPPP") is the most common procedure performed to treat OSA. The procedure involves removal of the palatine tonsils, with resection and/or repositioning of the uvula and soft palate. The procedure can increase the airway dimensions at the palate region but does not address obstruction well in the tongue region, the portion of the throat located more inferiorly.

A number of techniques and technologies have been developed to treat the tongue region. One approach utilizes radiofrequency energy to shrink and/or stiffen the soft palate and tongue. Radiofrequency energy can be used to create coagulative lesions at specific locations, and the healing process creates fibrosis and the associated tissue shrinkage and stiffening. Radiofrequency technologies can also be used to resect tongue tissue and reduce tongue size. Although effective in some, radiofrequency procedures have not performed well in the large majority of OSA patients.

Another OSA surgical approach to the tongue region is pulling the tongue anteriorly or otherwise preventing the posterior tongue prolapse that can occur with the loss of muscle tone during sleep. The most recent significant such surgical system was approved by the FDA in February 1998. Known as the tongue suspension or stabilization procedure (with the trade name Repose), it is intended to pull the tongue forward and/or stabilize the tongue in place, thereby keeping the tongue from falling into the airway during sleep. The system utilizes a bone screw inserted into the mandible. The screw attaches to a non-absorbable suture, which travels the length of the tongue and back. A similar application of this technique uses two bone screws attached to the mandible to pull the hyoid bone anteriorly and superiorly. Maxillomandibular advancement is an effective but highly invasive procedure, and the procedure's substantial morbidity and risks have limited its widespread adoption.

Techniques have also been developed for treating the soft palate with palatal implants. One attempt is a method for treating snoring of a patient, which includes embedding an implant into the patient's soft palate in order to alter the dynamic response of the soft palate to airflow. Other techniques and technologies rely on the use of chemical or thermal (including radiofrequency) injury of the soft palate to shrink and/or stiffen the palate, primarily to treat snoring but not OSA.

These treatments have demonstrated limited effectiveness and, in some cases, high morbidity, contribute to an ongoing need for more effective treatments for OSA and/or snoring.

SUMMARY OF THE INVENTION

To address the needs in the art, an orthotic obstructive sleep apnea treatment device is provided that includes a hyoid bone attachment element that is configured to attach a ferric element to a hyoid bone, where the ferric element faces along a treatment vector from the hyoid bone, and the treatment vector is oriented relative to a sagittal plane of a human subject, an external orthotic neck device, wherein the external orthotic neck device comprises a contoured housing having a shape disposed to conform about a i) neck, ii) head, iii) chest, i) and ii), i) and iii), or ii) and iii) of the human subject, wherein the contoured housing comprises a force delivery element, where the force delivery element is configured to be disposed at an exterior-front neck region of the human subject, where the force delivery element provides an attractive force to the ferric element along the treatment vector, where the housing is disposed to receive a removable the force delivery element inserted to a cavity in the housing, and a force sensor, where the force sensor measures a force that can include a force exerted on the hyoid bone, a skin contact pressure, tissue compression between the ferric element and the force delivery element, or a second force exerted by the force delivery element. Alternatively an accelerometer can be used in addition or instead of a force sensor, where the accelerometer measures kinematic variables or movement that can include kinematic variables or movement of the external orthotic neck device, the hyoid bone attachment element, the hyoid bone or tissues connected to the hyoid bone.

DETAILED DESCRIPTION

The current invention provides an external orthotic device for pulling on the hyoid bone using an internally implanted magnet attached to the hyoid. The device cradles an external magnet whereby the distance between the internal and external magnet can be adjusted by adjusting the external device, moving the cradled external magnet closer to or farther away from the implanted magnet, and thus adjusting the force applied to the hyoid.

The orthotic device has a shape or multiple shapes that fits a wide spectrum of anterior neck configurations. The shape of the device minimizes and/or avoids contact pressure over the hyoid bone and other structures that are secured directly to an internal ferric element. The ferric element could be either permanently magnetized (e.g. rare-earth magnets) or it could be a magnetically susceptible material that becomes magnetized when exposed to the magnetic field of the external device (e.g. a paramagnetic material such as steel).

According to the invention, the device is disposed to adjust the pull on the hyoid bone, where the pull is strong enough and in an appropriate direction to maintain airway patency.

In another aspect of the invention, the device is disposed to adjust the compression of tissue between the internal implanted magnet and the external device, where damage to the skin and subcutaneous tissue is avoided by restricting the compressive pressure between the two magnets. Further, the device is disposed to adjust the pressure exerted on tissue supporting the device, where the pressure is low enough to avoid damaging the tissue.

In another aspect of the invention, the device is disposed to sense the magnitude, direction and distribution of force imposed on the hyoid bone. By sensing minimum tension, and further sensing breathing or snoring, the device provides adjustability in the force imposed on the hyoid bone, where a single setting may not be appropriate over the long term, whether due to tissue edema, weight changes, sleeping position and breathing type, or other factors that can affect airway collapsibility.

The current invention provides for monitoring and adjusting different forces exerted on a patient, where these forces include: the force of pull on the hyoid such that it is equal to the elastic restoration forces on the hyoid at the required hyoid displacement; a compression pressure of tissue between the magnets or ferric elements, where the pressure is determined by the magnetic force divided by the surface area over which it is spread; and a surface pressure on tissue supporting the devices, where the total supporting force is equal to the required force of pull on the hyoid. Here, the pressure is equal to the force divided by the total surface area over which it is spread.

According to the invention, an important force or pressure to measure for safety is the compression of tissue between ferric elements. In some applications the external magnet may be close enough to the ferric element that the skin and subcutaneous tissue will be compressed between the two magnets. The maximum compressive pressure will occur at the minimum distance between the magnets, which will be determined by the strength of the magnets and the compressibility of the tissue. The current invention provides safety features that ensure this maximum compressive pressure be sufficiently low to avoid tissue damage, where the pressure is equal to the magnetic force divided by the surface area over which the force is spread.

As the external magnet is pulled away from the skin, the internal ferric element will move with it (hence maintaining the same compressive pressure) until the elastic restoration forces pulling the hyoid towards the hyoid's resting position are greater than the magnetic forces between the two magnets.

When the internal magnet has been pulled so far that the elastic restoration forces pulling the hyoid back towards its resting position are greater than the magnetic forces pulling the internal ferric element towards the external magnet, the two elements will start to be pulled apart. As the magnet is pulled farther away, the compression of tissue between the two magnets will decrease. Eventually, there will be no compression and the external magnet will lift off the skin. Eventually, the elastic restoration forces will exceed the forces of the external magnet acting on the internal ferric element (which falls off rapidly as $1/r^2$) and the hyoid will relax to its resting position.

The current invention addresses the instance, where, when the magnetic forces are greater than the pull force, the external magnet sits on the skin. The advantage of the invention is that the distance between the magnet and ferric element (and hence the forces) will be determined by the compressibility of the tissue and will be static in time.

The present invention uses the attraction between an implanted ferric material component and an external magnetic component to keep the airway open and prevent airway collapse. The external component includes a neck accessory that is readily placed or removed to make the device active or inactive, respectively. According to one embodiment an internal magnet and an external magnet are provided. In another embodiment, an internal ferric material and an external magnet are provided.

Figure 1:
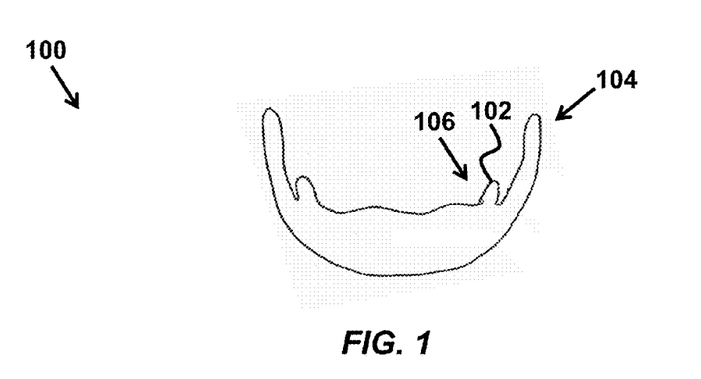
FIG. 1 shows a planar view of a hyoid bone

FIG. 1 shows a hyoid bone 100, which is a horseshoe shaped bone situated in the anterior midline of the neck between the chin and the thyroid cartilage. The hyoid bone 100 is a very unique bone, solitary in design, and is the only bone in the human body that does not attach to any other bone. The hyoid bone 100 is located below the mandible and is located in the mid portion of the neck, superior to the larynx and suspended from the styloid process 102 of the temporal bone via the stylohyoid muscles and ligaments. The hyoid bone has of its body, two posteriorly projecting greater cornua 104 which attach to these ligaments, and two lesser cornua 106 which are located more anteriorly.

The hyoid bone 100 has extensive soft tissue attachments throughout the area, including those to the tongue, epiglottis, and lateral pharyngeal tissues around the throat. The multiple muscle attachments that connect the hyoid bone 100 to these and other structures include the hyoglossus, mylohyoid, sternohyoid, and thyrohyoid muscles, and the hyoepiglottic ligament connects the hyoid to the epiglottis. The attachments between the hyoid bone 100 and other structures of the head and neck enable forces applied to the hyoid bone 100 to be applied to these other structures indirectly.

Figure 2A:
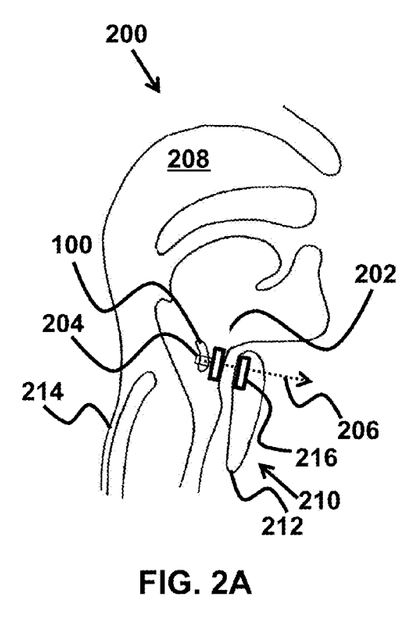
FIGS. 2A-2B show planar schematic views an orthotic obstructive sleep apnea treatment device, according to one embodiment of the invention.
Figure 2B:
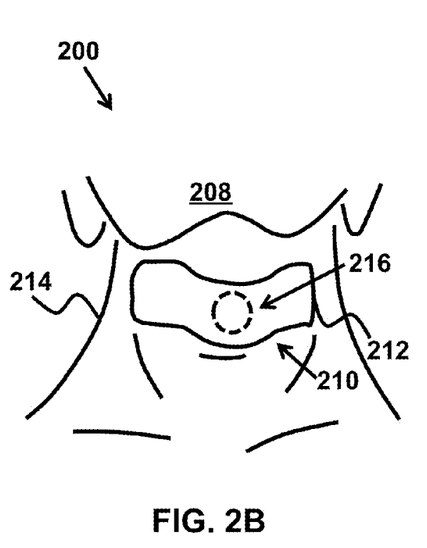

FIGS. 2A-2B show planar schematic views of one embodiment of an orthotic obstructive sleep apnea treatment device 200, where a ferric element 202 (shown in FIG. 2A) is attached to the hyoid bone 100 using an attachment element 204. According to one aspect of the invention, the ferric element 202 (shown in FIG. 2A) is disposed to face along a treatment vector 206 from the hyoid bone 100, and the treatment vector is oriented relative to a sagittal plane of a human subject 208.

As shown in FIGS. 2A and 2B, the orthotic obstructive sleep apnea treatment device 200 further includes an external orthotic neck device 210 having a contoured housing 212 with a shape disposed to conform about a neck 214 of the human subject 208, where the housing 212 includes a force delivery element 216 disposed at an exterior-front neck region 220 of the human subject 208 and is disposed to provide an attractive force to the ferric element 204 along the treatment vector 206. According to one aspect of the invention, the patient 208 can prevent or relieve airway obstruction by wearing the neck accessory 210, with its magnetic external component 216, where the external component 216 acts on the internal component 202 through magnetic force. The internal magnetic component 202 is secured to the hyoid bone 100, so moving the internal component 202 causes a corresponding movement of the hyoid bone 100. In a further aspect of the invention, the magnetic attraction between the internal component 202 and the external component 216 is disposed to not block the airway at any point due to misalignment.

Figure 3A:
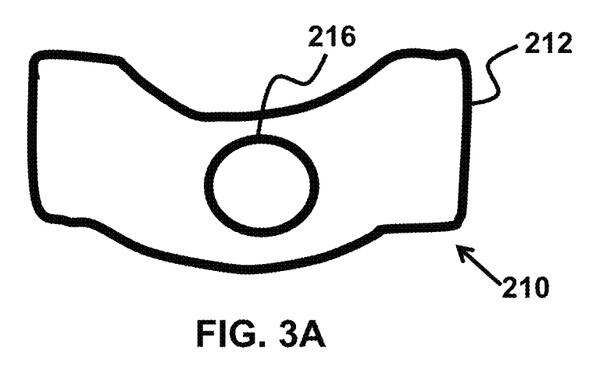
FIGS. 3A-3B show some exemplary embodiments of the external orthotic neck device, according to the current invention.
Figure 3B:
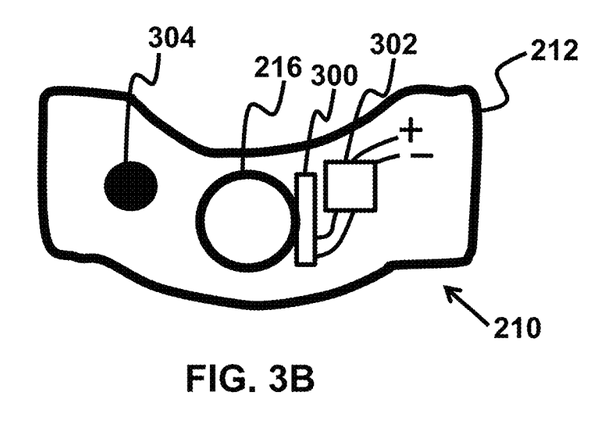

FIGS. 3A and 3B show some exemplary embodiments of the external orthotic neck device 210, where FIG. 3A shows the contoured housing 212 holding the force delivery element 216, and FIG. 3B shows the contoured housing 212 holding the force delivery element 216 and further includes a force sensor 300 disposed to measure a force exerted on the hyoid bone 100, a skin contact pressure, tissue compression between the ferric element and the force delivery element, or any combination thereof. Alternatively an accelerometer 300 can be used in addition or instead of a force sensor 300, where the accelerometer measures kinematic variables or movement that can include kinematic variables or movement of the external orthotic neck device, the hyoid bone attachment element, the hyoid bone or tissues connected to the hyoid bone. According to one aspect of the invention, the housing 212 includes an appropriately programmed microprocessor and memory device 302 disposed to monitor data from sensor 300, where the microprocessor and memory device 302 outputs measurement data according to time. In a further aspect the housing includes a visual display 304, where the microprocessor and memory device 302 outputs the measurement data to the visual display 304. Here the visual display 304 can include indicator lights that provide acceptable or unacceptable display signals according to readings from sensor 300.

Figure 4A:
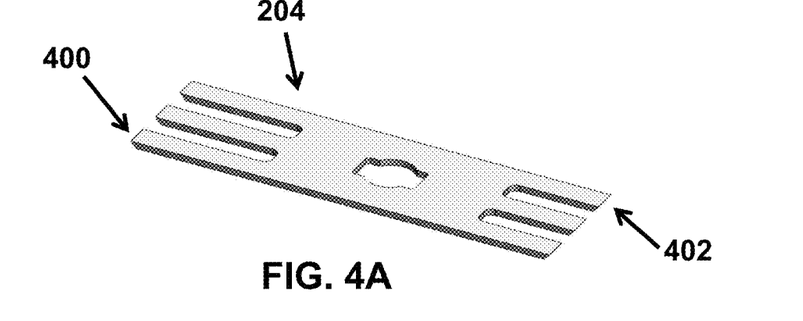
FIGS. 4A-4C show an exemplary attachment element to secure implant device to the hyoid bone, according to one embodiment of the invention.
Figure 4B:
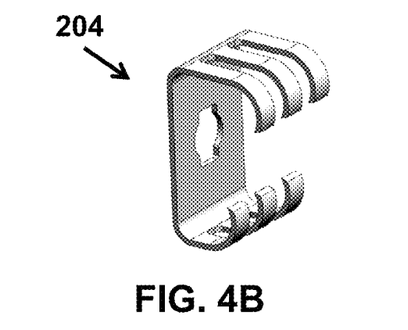
Figure 4C:
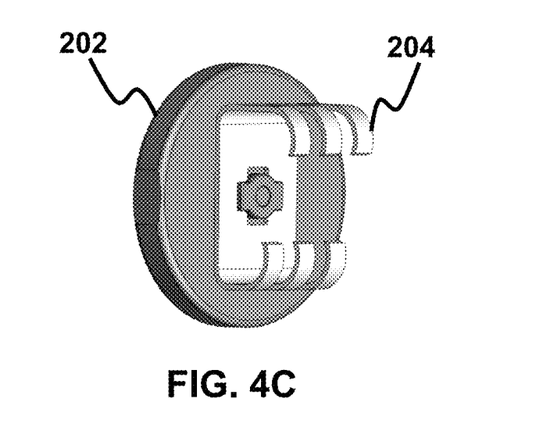

An exemplary attachment element 204 to secure implant device to the hyoid bone 100 is shown in FIGS. 4A-4C. As shown in FIGS. 4B and 4C, the clip 204 geometry matches that of the body of the hyoid bone 100 in order to create the best fit and hold on the bone 100. Superior clip arm 400 (shown in FIG. 4A) is longer than inferior clip arm 402 (shown in FIG. 4A) to accommodate the larger bone thickness superiorly. Attachment onto the center of the body of the hyoid 100, as opposed to the Cornu (horns 102/104) or the sides of the body, permit the smallest incision for implantation and the most regularity between patients.

FIG. 4A shows "fingers" 404 cut into the clip 204, where the clip 204 goes around the hyoid 100 and into tissue, prevent excess tissue damage while still providing adequate fixation. In one aspect, the clip 204 can be made of Nitinol material to aid in implantation. In another aspect, the clip 204 can utilize either the super elastic property or temperature shape memory property of Nitinol. To use the super elastic property a tool is used to stretch the clip 204 open to pass over the Hyoid 100. The implantation tool is then relaxed and the clip 204 springs back to its original shape, securing it around the Hyoid bone 100. In another aspect, the temperature shape memory property is used, there the clip 204 is cooled (possibly in an ice bath) and deformed while cool into a shape that will easily fit over the hyoid 100. The clip 204 is then placed on the hyoid 100 and as the heat from the patient 208 warms the clip 204, it reforms back to its original shape and is secured around the hyoid 100.

Figure 5A:
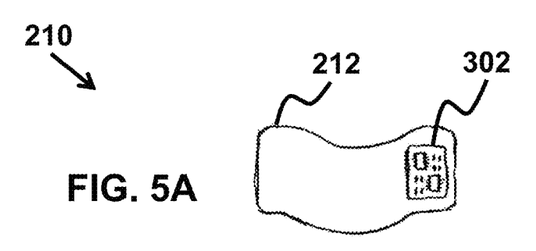
FIGS. 5A-5C show other exemplary embodiments of the invention.
Figure 5B:
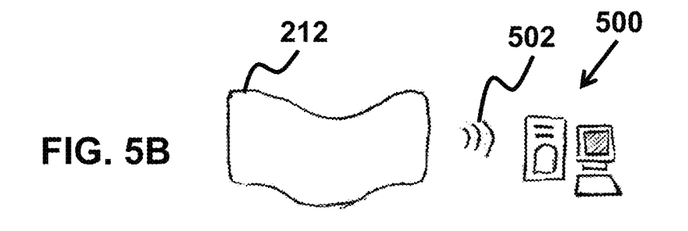
Figure 5C:
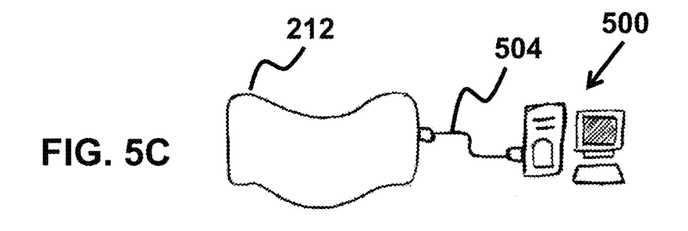

FIGS. 5A-5C show other exemplary embodiments of the external orthotic neck device invention, where the force delivery element 216 in the housing 210 includes an adjustable force. Here, the force delivery element 216 can include an appropriately programmed microprocessor and memory 302, where the data from sensor 300 is processed through the appropriately programmed microprocessor and memory 302, and the force is adjusted according to instructions from the appropriately programmed microprocessor and memory 302. Here, the force is adjusted discretely or continuously. In one aspect, the microprocessor and memory device 302 is disposed to provide pattern recognition, where for the pattern recognition, the patterns are not indicative of the quality of sleep, and the current invention recognizes patterns associated with breathing, forces, and other things. In another aspect, the recognized pattern is output to an appropriately programmed computer 500 for analysis. In a further aspect, the force is adjusted according to the recognized pattern. In yet another aspect, the force delivery element 216 includes an electromagnet, where the attractive force is adjusted according to an electrical current. Further, the strength of the electrical current is according to data from sensor 300. Additionally, the strength of the electrical current is according to a predetermined pattern, wherein the predetermined pattern comprises data from a pattern analysis.

In another aspect of the invention, the housing includes connectivity to an appropriately programmed external computer and data storage device 500, where the connectivity includes wired connectivity 504 or wireless connectivity 504, and where data from sensor 300 is communicated to and from the appropriately programmed computer and external data storage device 500. Further, the sensor data could be communicated via phone system for tracking and/or analysis. In particular, the sensors could be transmitted via Bluetooth to a cell phone (the memory and microprocessor) and then on to the 'cloud'.

Figure 6:
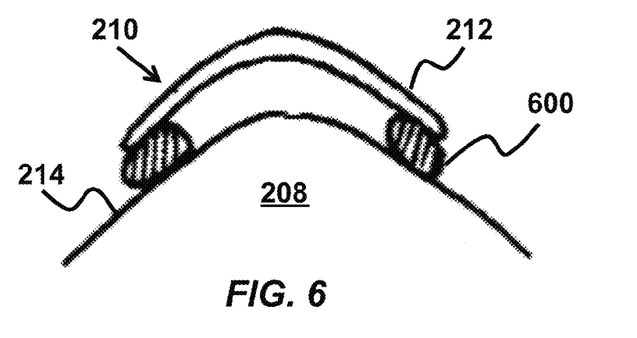
FIG. 6 shows a housing that includes an inflatable balloon bladder disposed to conform about the neck of a patient, according to the current invention.

FIG. 6 shows a further aspect of the invention, where the housing 212 includes an inflatable balloon bladder 600 disposed to conform about the neck of a patient 208. In one aspect, the inflatable balloon bladder 600 includes a discrete lumen for localized shape adjustment. In another aspect, the force delivery element 216 includes an appropriately programmed microprocessor and memory 302, where the data from sensor 300 is processed through the appropriately programmed microprocessor and memory 302, where the inflatable balloon bladder 600 is adjusted according to data from sensor 300. In another aspect, the inflatable balloon bladder 600 is filled with air, foam or gel.

Figure 7A:
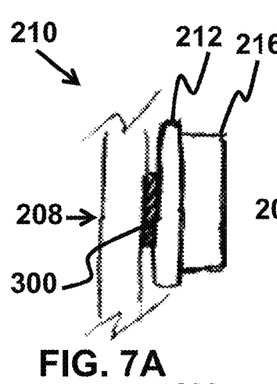
FIGS. 7A-7F show some exemplary embodiments of the external orthotic neck device, according to the current invention.
Figures 7B, 7C:
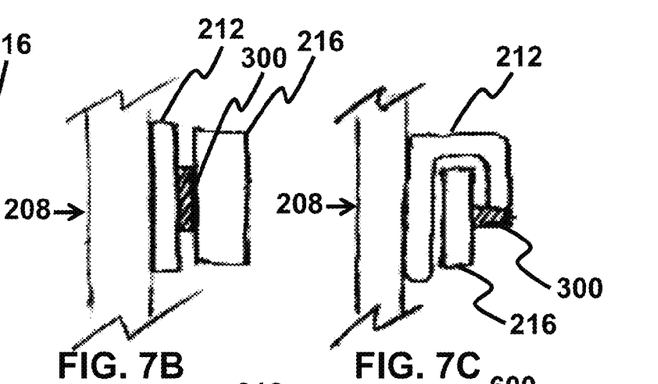
Figure 7D:
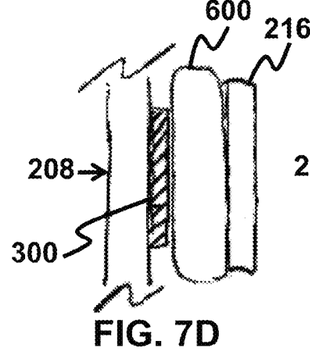
Figures 7E, 7F:
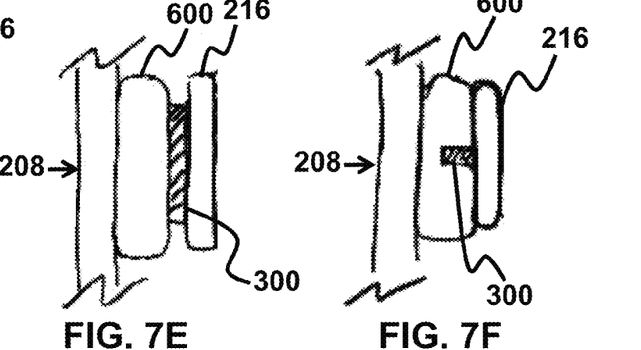

FIGS. 7A-7F show some exemplary embodiments of sensors in the external orthotic neck device 210. FIG. 7A shows the external orthotic neck device 210 having a force delivery element 216 disposed on the housing 212, and the sensor 300 disposed on the skin of the patient 208. FIG. 7B shows the external orthotic neck device 210 having a force delivery element 216 disposed on sensor 300, and the housing 212 disposed between sensor 300 and the skin of the patient 208. FIG. 7C shows a housing 212 disposed to suspend sensor 300 and force delivery element 216 with the housing 212 and the housing 212 is disposed in the skin of the patient 208. FIG. 7D shows the external orthotic neck device 210 having a force delivery element 216 disposed on the inflatable balloon bladder 600, and sensor 300 disposed between the inflatable balloon bladder 600 and the skin of the patient 208. FIG. 7E shows the external orthotic neck device 210 having a force delivery element 216 disposed on sensor 300, and the inflatable balloon bladder 600 disposed between sensor 300 and the skin of the patient 208. FIG. 7F shows the inflatable balloon bladder 600 disposed between the skin of the patient 208 and the housing 212, where sensor 300 is disposed in the inflatable balloon bladder 600. Further, a temperature sensor may be provided to measure compliance (hours of use) of the device.

Figure 8A:
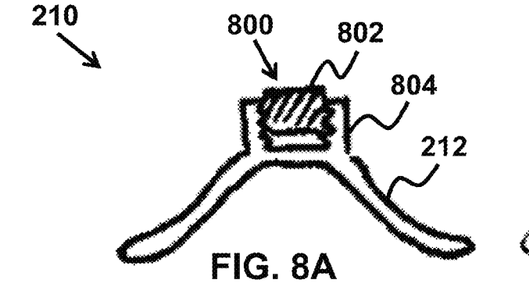
FIGS. 8A-8D show the housing having an exemplary embodiment of an adjustable force delivery element, according to the current invention.
Figure 8B:
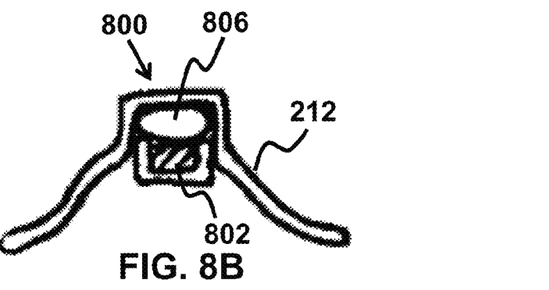
Figure 8C:
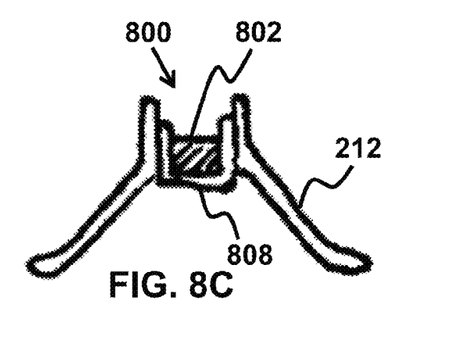
Figure 8D:
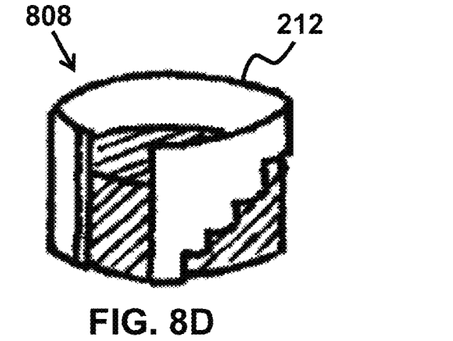

In yet another aspect of the invention, the force delivery element 216 includes an adjustable force, wherein the adjustable force includes a moveable magnet. FIGS. 8A-8D show the housing 212 having an exemplary embodiment of an adjustable force delivery element 800, where FIG. 8A shows an adjustable magnet 802 disposed in a threaded positioning element 804. FIG. 8B shows an adjustable magnet 802 disposed to move according to an inflatable bladder 806, and FIG. 8C shows an adjustable magnet 802 disposed in an indexed positioning element 808. FIG. 8D shows an example of the adjustable magnet 802 disposed in an indexed positioning element 808.

Figure 9A:
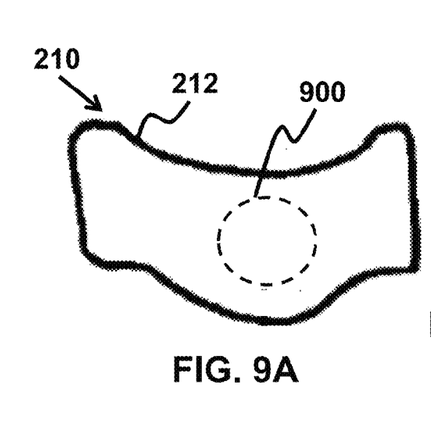
FIGS. 9A-9D show an exemplary housing disposed to receive force delivery elements, according to the current invention.
Figures 9B, 9C:
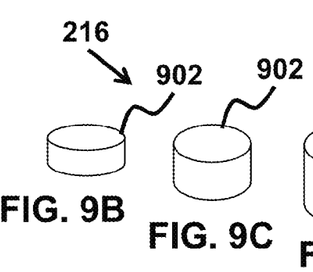
Figure 9D:
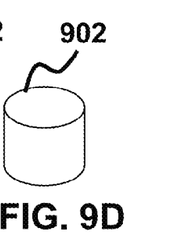

FIGS. 9A-9D show a housing 212 disposed to receive force delivery elements 216 that can be inserted to a cavity 900 in the housing 212. FIGS. 9B-9D show the force delivery element 216 includes a removable magnet, where the housing 212 for the force delivery element is disposed to receive magnets 902 having different magnetic forces. Here the magnets 902 can include different shapes, sizes or materials.

In another aspect of the invention, the force delivery element includes an adjustable magnet disposed to change the treatment vector, where the treatment vector includes a force and a direction.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, features of this orthotic device could be applied to treat other diseases and conditions. Possible applications include orthotic devices worn on the torso to apply force to internal magnet(s) on the stomach, bladder or rectum. The direction and magnitude of these forces could be used to alleviate hunger, acid reflux, urination or defecation. Similarly, the force could be use for pain relief by applying force to painful structures in the body.

There are many possible variations in the detailed design of the magnets that could affect the magnitude and direction of the magnetic field. Sample variations would include the use of Hallbach arrays, back iron or pole pieces to focus the field. Assemblies with other ferromagnetic materials could increase or reduce the strength of the magnetic field and change the directional characteristics of the magnet system.

All such variations are considered to be within the scope and spirit of the present invention as defined by the following claims and their legal equivalents.

What is claimed:

1. An orthotic obstructive sleep apnea treatment device, comprising:
   (a) a hyoid bone attachment element that is configured to attach a ferric element to a hyoid bone, wherein said ferric element faces along a treatment vector from said hyoid bone, wherein said treatment vector is oriented relative to a sagittal plane of a human subject;
   (b) an external orthotic neck device, wherein said external orthotic neck device comprises a contoured housing having a shape disposed to conform about a i) neck, ii) head, iii) chest, i) and ii), i) and iii), or ii) and iii) of said human subject, wherein said contoured housing comprises a force delivery element, wherein said force delivery element is configured to be disposed at an exterior-front neck region of said human subject, wherein said force delivery element provides an attractive force to said ferric element along said treatment vector; and
   (c) the contoured housing further comprising an accelerometer, wherein said accelerometer measures kinematic variables or movement from the group consisting of kinematic variables or movement of the external orthotic neck device, the hyoid bone attachment element, the hyoid bone, and one or more tissues connected to the hyoid bone.

2. The orthotic obstructive sleep apnea treatment device of claim 1, wherein said contoured housing comprises a microprocessor and a memory device, wherein said microprocessor and said memory device are disposed to monitor data from said accelerometer, wherein said microprocessor and said memory device outputs measurement data according to time.

3. The orthotic obstructive sleep apnea treatment device of claim 2, wherein said contoured housing comprises a visual display, wherein said microprocessor and said memory device outputs said measurement data to said visual display.

4. The orthotic obstructive sleep apnea treatment device of claim 3, wherein said visual display comprises indicator lights, wherein said indicator lights provide acceptable or unacceptable display signals according to readings from said accelerometer.

5. The orthotic obstructive sleep apnea treatment device of claim 1, wherein said contoured housing comprises connectivity to an external computer and a data storage device, wherein said connectivity comprises wired connectivity or wireless connectivity, wherein data from said accelerometer is communicated to and from said external computer and said external data storage device.

6. The orthotic obstructive sleep apnea treatment device of claim 1, wherein said force delivery element comprises an adjustable force, wherein said force delivery element comprises a microprocessor and a memory device, wherein data from said accelerometer is processed through said microprocessor and said memory device, wherein said adjustable force is adjusted according to instructions from said microprocessor and memory.

7. The orthotic obstructive sleep apnea treatment device of claim 6, wherein said adjustable force is adjusted discretely or continuously.

8. The orthotic obstructive sleep apnea treatment device of claim 6, wherein said microprocessor and memory are configured to provide pattern recognition.

9. The orthotic obstructive sleep apnea treatment device of claim 8, wherein a recognized pattern from said pattern recognition is configured to be output for analysis.

10. The orthotic obstructive sleep apnea treatment device of claim 8, wherein said adjustable force is configured according to said recognized pattern.

11. The orthotic obstructive sleep apnea treatment device of claim 8, wherein said force delivery element comprises an electromagnet, wherein an attractive force exerted by said electromagnet is capable of being adjusted according to an electrical current.

12. The orthotic obstructive sleep apnea treatment device of claim 11, wherein an amperage of said electrical current is determined according to data from said accelerometer.

13. The orthotic obstructive sleep apnea treatment device of claim 11, wherein an amperage of said electrical current is determined according to a predetermined pattern, wherein said predetermined pattern comprises data from a pattern analysis.

14. The orthotic obstructive sleep apnea treatment device of claim 1, wherein said force delivery element comprises an adjustable force element, wherein said adjustable force element comprises a moveable magnet.

15. The orthotic obstructive sleep apnea treatment device of claim 1, wherein said force delivery element comprises a removable magnet, wherein said force delivery element is disposed to receive magnets having different magnetic forces.

16. The orthotic obstructive sleep apnea treatment device of claim 15, wherein said magnets comprise different shapes, sizes or materials.

17. The orthotic obstructive sleep apnea treatment device of claim 1, wherein said contoured housing comprises an inflatable balloon bladder, wherein said inflatable balloon bladder is disposed to conform about said neck.

18. The orthotic obstructive sleep apnea treatment device of claim 17, wherein said inflatable balloon bladder comprises a discrete lumen for localized shape adjustment.

19. The orthotic obstructive sleep apnea treatment device of claim 17, wherein said force delivery element comprises a microprocessor and a memory device, wherein data from said accelerometer is configured to be processed through said microprocessor and said memory device, wherein said inflatable balloon bladder is configured to be adjusted according to said data from said accelerometer.

20. The orthotic obstructive sleep apnea treatment device of claim 17, wherein said inflatable balloon bladder is filled with air, foam or gel.

21. The orthotic obstructive sleep apnea treatment device of claim 1, wherein said force delivery element comprises an adjustable magnet, wherein said adjustable magnet is disposed in a threaded positioner.

22. The orthotic obstructive sleep apnea treatment device of claim 1, wherein said force delivery element comprises an adjustable magnet, wherein said adjustable magnet is disposed in an indexed positioner.

23. The orthotic obstructive sleep apnea treatment device of claim 1, wherein said force delivery element comprises an adjustable magnet, wherein said adjustable magnet is disposed to change the treatment vector, wherein said treatment vector comprises a force and a direction.

* * * * *